United States Patent [19]

Mikhail

[11] Patent Number: 5,683,395
[45] Date of Patent: Nov. 4, 1997

[54] SYSTEM FOR PERFORMING HIP PROTHESIS REVISION SURGERY

[76] Inventor: W. E. Michael Mikhail, 4203 Shamley Green, Toledo, Ohio 43623

[21] Appl. No.: 638,607

[22] Filed: Apr. 26, 1996

[51] Int. Cl.$^6$ .................................................. A61F 2/28
[52] U.S. Cl. .................. 606/86; 606/92; 606/95; 623/23
[58] Field of Search .................... 606/89, 95, 99, 606/100, 86, 63, 65; 623/22, 23; 403/230; 285/317.1, 321; 248/74.1, 74.2; 411/352, 353, 522, 516, 517, 940, 946, 618

[56] References Cited

U.S. PATENT DOCUMENTS

| | | | |
|---|---|---|---|
| 4,341,206 | 7/1982 | Perrett et al. | 128/92 |
| 4,399,814 | 8/1983 | Pratt, Jr. et al. | 128/92 |
| 4,623,353 | 11/1986 | Buechel et al. | 623/23 |
| 4,678,471 | 7/1987 | Noble et al. | 623/16 |
| 4,686,972 | 8/1987 | Kurland | 128/92 |
| 4,706,659 | 11/1987 | Matthews et al. | 128/92 |
| 4,751,922 | 6/1988 | DiPietropolo | 128/92 |
| 4,815,454 | 3/1989 | Dozier, Jr. | 128/92 |
| 4,846,161 | 7/1989 | Roger | 128/92 |
| 4,860,735 | 8/1989 | Davey et al. | 128/92 |
| 4,865,608 | 9/1989 | Brooker, Jr. | 623/23 |
| 4,873,969 | 10/1989 | Huebsch | 128/92 |
| 4,881,536 | 11/1989 | Noble et al. | 606/94 |
| 4,896,662 | 1/1990 | Noble | 606/94 |
| 4,919,153 | 4/1990 | Chin | 606/93 |
| 4,919,673 | 4/1990 | Willert et al. | 623/23 |
| 4,919,679 | 4/1990 | Averill et al. | 623/23 |
| 4,963,155 | 10/1990 | Lazzeri et al. | 623/23 |
| 4,986,826 | 1/1991 | Roger | 606/82 |
| 4,994,085 | 2/1991 | Sawai et al. | 623/23 |
| 5,015,817 | 5/1991 | Kranz | 623/22 |
| 5,021,063 | 6/1991 | Täger | 623/23 |
| 5,047,035 | 9/1991 | Mikhail et al. | 606/93 |
| 5,047,061 | 9/1991 | Brown | 623/23 |
| 5,061,287 | 10/1991 | Feiler | 623/16 |
| 5,078,746 | 1/1992 | Garner | 623/16 |
| 5,085,548 | 2/1992 | Moyles | 411/522 |
| 5,108,405 | 4/1992 | Mikhail et al. | 606/96 |
| 5,116,377 | 5/1992 | Skripitz | 623/23 |
| 5,192,282 | 3/1993 | Draenert | 606/65 |
| 5,192,283 | 3/1993 | Ling et al. | 606/93 |
| 5,197,841 | 3/1993 | Tanaka | 411/353 |
| 5,201,769 | 4/1993 | Schutzer | 623/23 |
| 5,314,489 | 5/1994 | Hoffman et al. | 623/22 |
| 5,443,469 | 8/1995 | Smith | 606/86 |
| 5,470,336 | 11/1995 | Ling et al. | 606/95 |
| 5,480,452 | 1/1996 | Hofmann et al. | 623/23 |
| 5,507,830 | 4/1996 | De Mane et al. | 623/23 |

FOREIGN PATENT DOCUMENTS

| | | |
|---|---|---|
| 2615097 | 5/1987 | France . |
| 0 315 283 | 11/1988 | United Kingdom . |
| 920993 | 3/1992 | WIPO | 606/89 |

OTHER PUBLICATIONS

Waldes Truarc Retaining Rings, Jan. 1981, p. 5 (Selector Guide).

Kenneth J. Hock, M.D., "Economy is the Mother of a Cement Removal Technique", Orthopedics Today, pp. 18–19.

John N. Insall, M.D., et al., "Principles and Techniques of Knee Replacement", published in 1983 by New York Society for the Relief of the Ruptured and Crippled, pp. 20–21.

John Insall, M.D. and Albert H. Burstein, Ph.D., "Insall/ Burstein™ Total Knee System" Pamphlet.

W.E. Michael Mikhail, M.D. and Lars Weidenhielm, M.D., "The CPT Hip Prosthesis" Pamphlet (1994).

*Primary Examiner*—Michael Buiz
*Assistant Examiner*—Julian W. Woo
*Attorney, Agent, or Firm*—Emch, Schaffer, Schaub & Porcello Co., L.P.A.

[57] ABSTRACT

A cannulated tamp having a proximal compressive flange as used for compacting bone graft material in a femur having a cavity being prepared to receive a femural prosthesis. The tamp of the present invention is particularly useful in achieving uniform compaction in the proximal area of the femur. The compressive flange may be monolithic with the stem of the tamp or may be a separate modular member affixed thereto. Under one embodiment a series of passageways are provided for attachment to a source of vacuum for evacuating blood and other fluids from the prepared cavity.

38 Claims, 9 Drawing Sheets

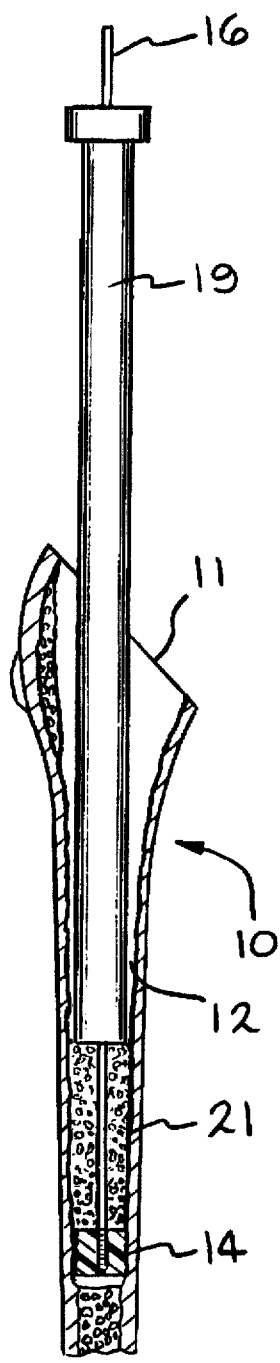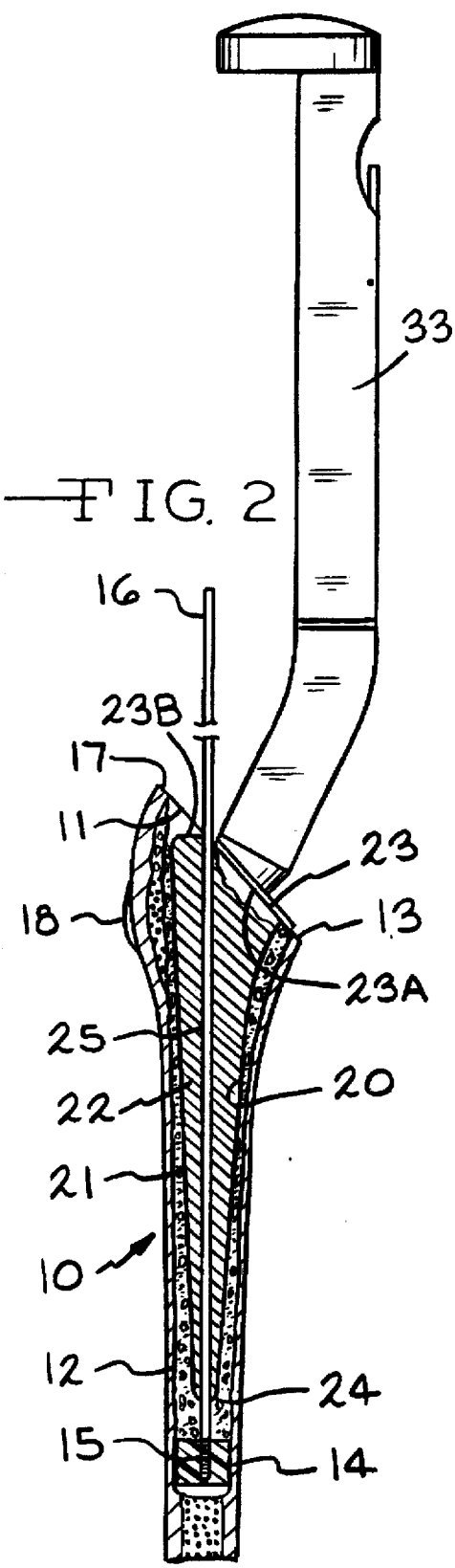

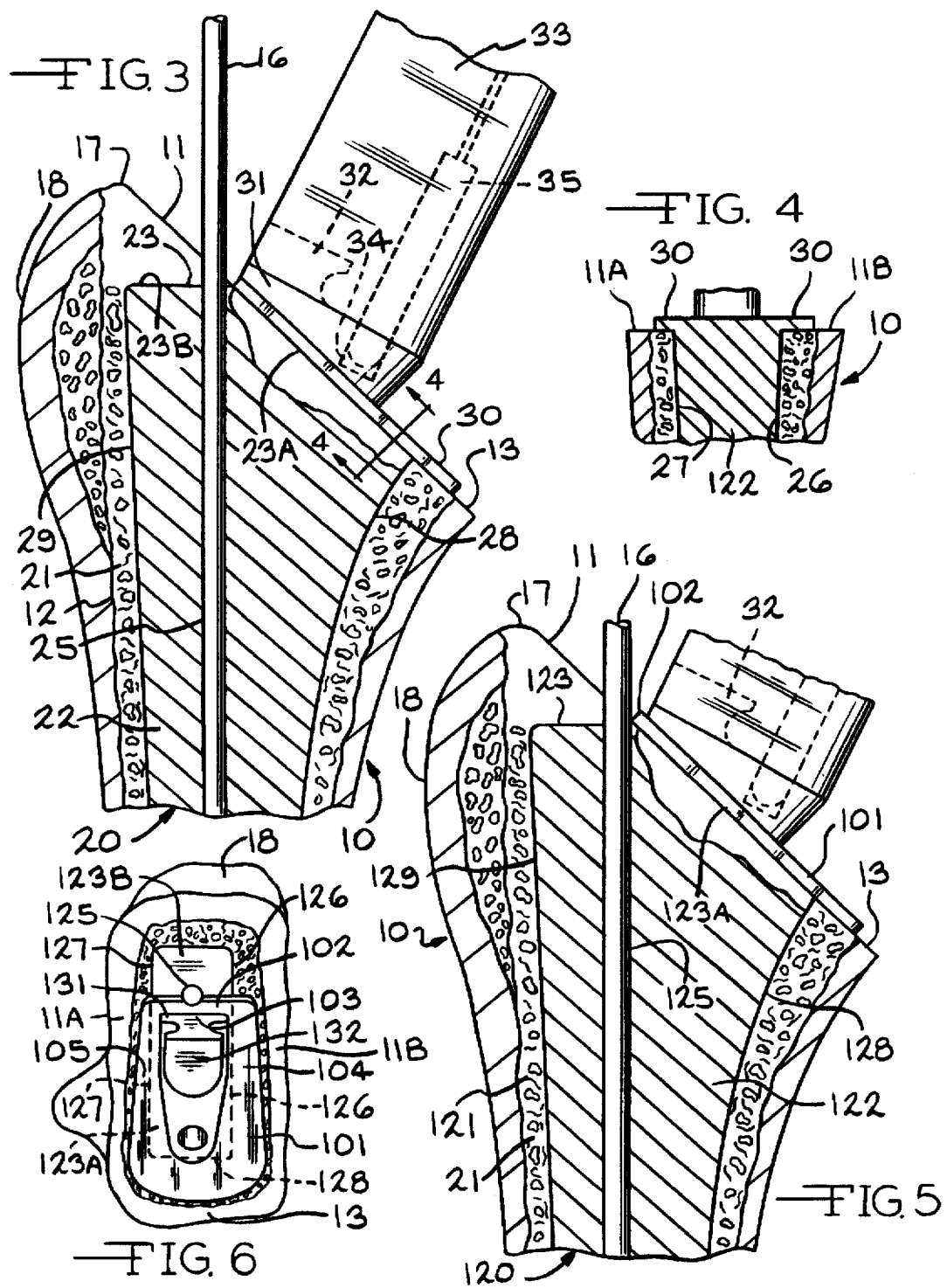

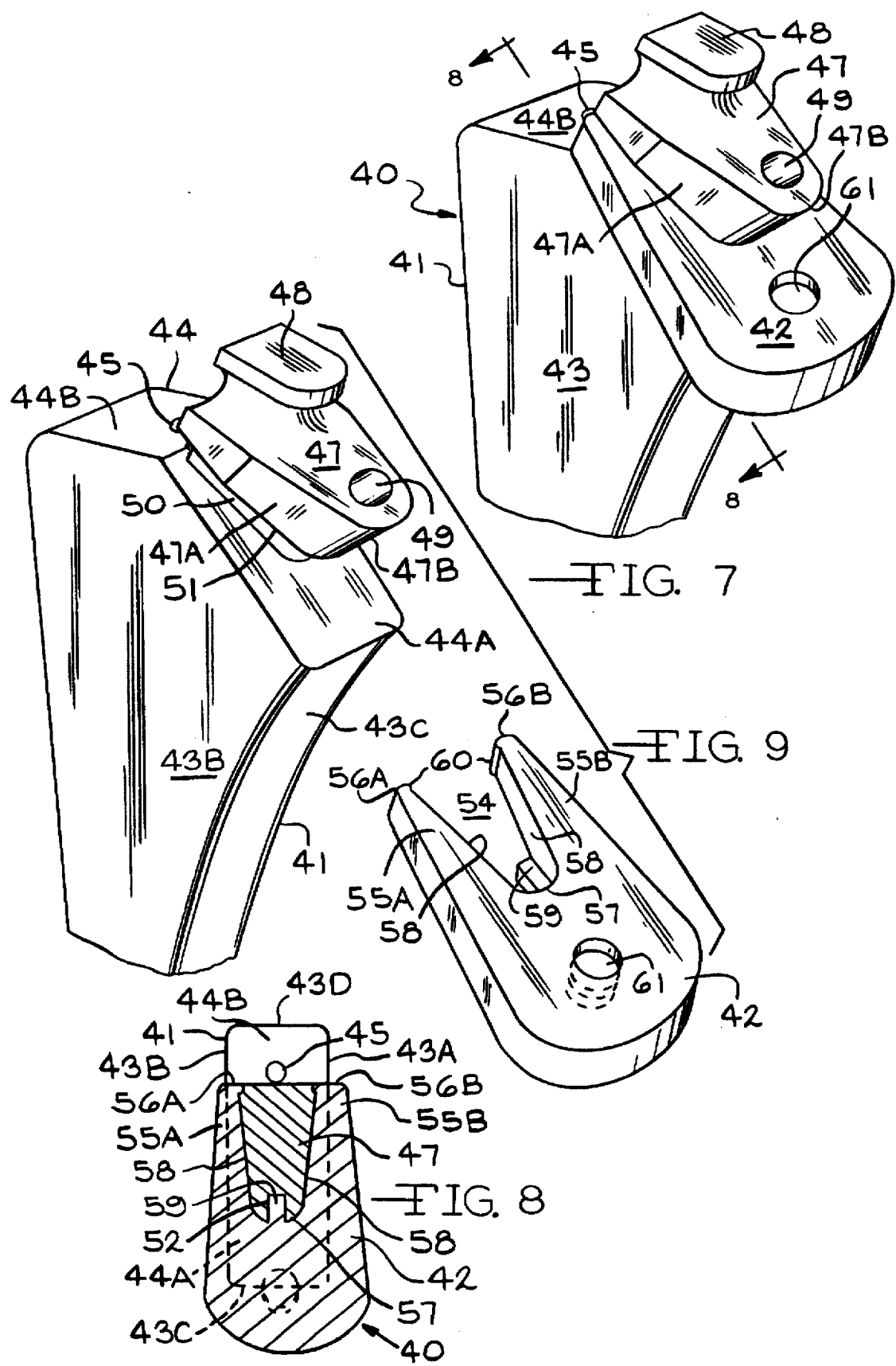

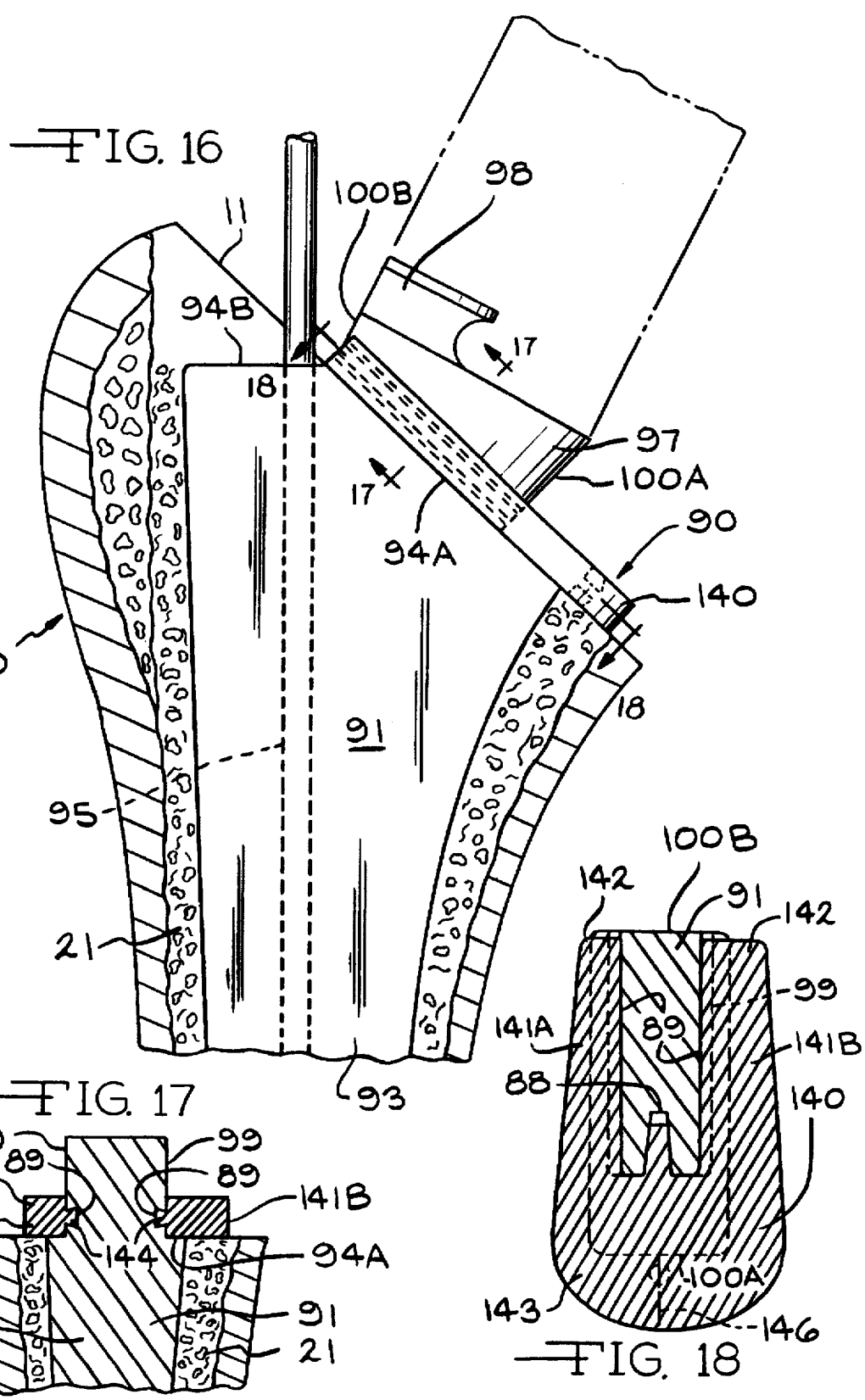

SYSTEM FOR PERFORMING HIP PROTHESIS REVISION SURGERY

BACKGROUND ART

U.S. Pat. Nos. 5,192,283 and 5,470,336, for which I am a co-inventor, are directed to a method and apparatus for performing hip prosthesis revision surgery which includes preparation of the enlarged cavity left after removal of the original prosthesis. A tamp having a longitudinal passageway extending longitudinally through the stem portion thereof and a guide wire positioned in the cavity function to compact bone graft material in the enlarged cavity and form a contoured cavity for receiving the new hip prosthesis. The tamp disclosed in such patents provides good compaction of the bone graft material contacted by the tapered stem from the distal end to an area somewhat spaced from the proximal end. However, the tamp disclosed in such prior art patents has no ability to provide compaction for bone graft material in the vicinity of the proximal end of the femur.

In performing hip revision surgery, it is desirable that the bone graft material be compacted uniformly throughout up to the proximal end of the femur. Prior to the present invention, the surgeon was forced to rely upon manually manipulated small metal compactors to compact the bone graft material in the area of such proximal end. The contact between such compactors and the bone graft material is very localized with the result that bone graft material adjacent the compactor bulges outwardly. As can be readily appreciated, this greatly hinders any chance of obtaining uniform packing and compression of bone graft material in the area of the proximal end. Many of the small metal compactors are sized to fit in the small gaps between the tamp and the bone. The use of the prior art small metal compactors in the gaps between the tamp and the bone, provides a substantial risk of damage to the femoral bone in that area, including danger of damaging the thin proximal end of the femur, the cortices of which have been compromised by prior total hip surgeries.

DISCLOSURE OF THE INVENTION

The present invention is an improvement over the inventions described and claimed in the above-identified patents. Under the present invention, the cannulated tamp is provided with an integral or a modular compressive flange. As with the tamp of the above-identified patents, the tamp as disclosed and claimed herein may be used in combination with a guide wire which maintains the tamp properly positioned in the cavity resulting from removal of the previously implanted prosthesis and any old bone cement and particulate debris. The tamp of the present invention has a tapered stem portion, preferably double tapered, and a proximal compressive flange with a distally facing bone graft compacting surface. The utilization of the tamp of the present invention with its proximal compressive flange provides compaction of bone graft material in the area of the proximal end of the femur being prepared to receive a new prosthesis as well as compaction in the other areas contacted by the tapered stem. The utilization of the proximal compressive flange with the tapered tamp provides superior compaction for the morsellized bone graft material in forming the cavity to receive the new hip joint prosthesis, particularly in the proximal area of the femur in addition to effective axial as well as uniform outward compression.

A series of varying sizes of tamps may be utilized to progressively reduce the size of the cavity to the final prepared size for implantation of a femoral prosthesis. If the femoral prosthesis is of a type requiring the use of bone cement, the cavity should have a size sufficient to allow for a cement mantle of 2 to 4 millimeters around the prosthesis. The compressive flange functions to compact morsellized bone graft material in the proximal area substantially level with the cortices of the femur. In the largest size, the compressive flange may be sized to overlie and contact the proximal end of the femur during compaction of the bone graft material to bring the uniformly compacted bone graft material substantially level with such proximal end and the cortices compromised from previous surgeries without damaging them or the greater trochanter.

The cannulated tamp with the proximal compressive flange can be used for revision surgery in which it is intended to implant either a collared or collarless prosthesis and either a prosthesis requiring the use of cement or a cementless type of prosthesis. The tamp may under the different embodiments disclosed herein have a flange which is integral and monolithic with the stem or have a separately formed, modular flange which modular flange may be one-piece or two-piece.

The disclosure of the above-identified two U.S. patents of which I am a co-inventor are incorporated herein by reference.

BRIEF DESCRIPTION OF THE DRAWINGS

FIG. 1 is an elevational view, partly in section, showing compaction of bone graft material in the distal area of a femoral cavity using a cylindrical tamp.

FIG. 2 is an elevational view, partly in section, showing the tamp system of the present invention for compacting morsellized bone graft to define a cavity prepared to receive a femoral prosthesis utilizing the method and apparatus of the present invention.

FIG. 3 is an enlarged fragmentary view of the proximal end of the tamp of FIG. 2 with an integral, monolithic compressive flange compacting morsellized bone graft material at the proximal end of a femur.

FIG. 4 is a fragmentary sectional view taken through line 4—4 of FIG. 3.

FIG. 5 is a view similar to FIG. 3 showing a modified embodiment.

FIG. 6 is a view looking toward the proximal end of a femur in which is positioned the tamp of the embodiment of FIG. 5.

FIG. 7 is a fragmentary perspective view of the proximal end of a modified cannulated tamp assembly showing the tamp member with a modular compressive flange member attached thereto.

FIG. 8 is a sectional view taken through line 8—8 of FIG. 7.

FIG. 9 is a fragmentary perspective view of the embodiment of FIG. 7 showing the modular compressive flange detached from the tamp member.

FIG. 16 is a view similar to FIG. 10 showing yet another embodiment.

FIG. 17 is a sectional view taken through line 17—17 of FIG. 16.

FIG. 18 is a sectional view taken through line 18—18 of FIG. 16.

BEST MODE OF CARRYING OUT INVENTION

Figure 10:
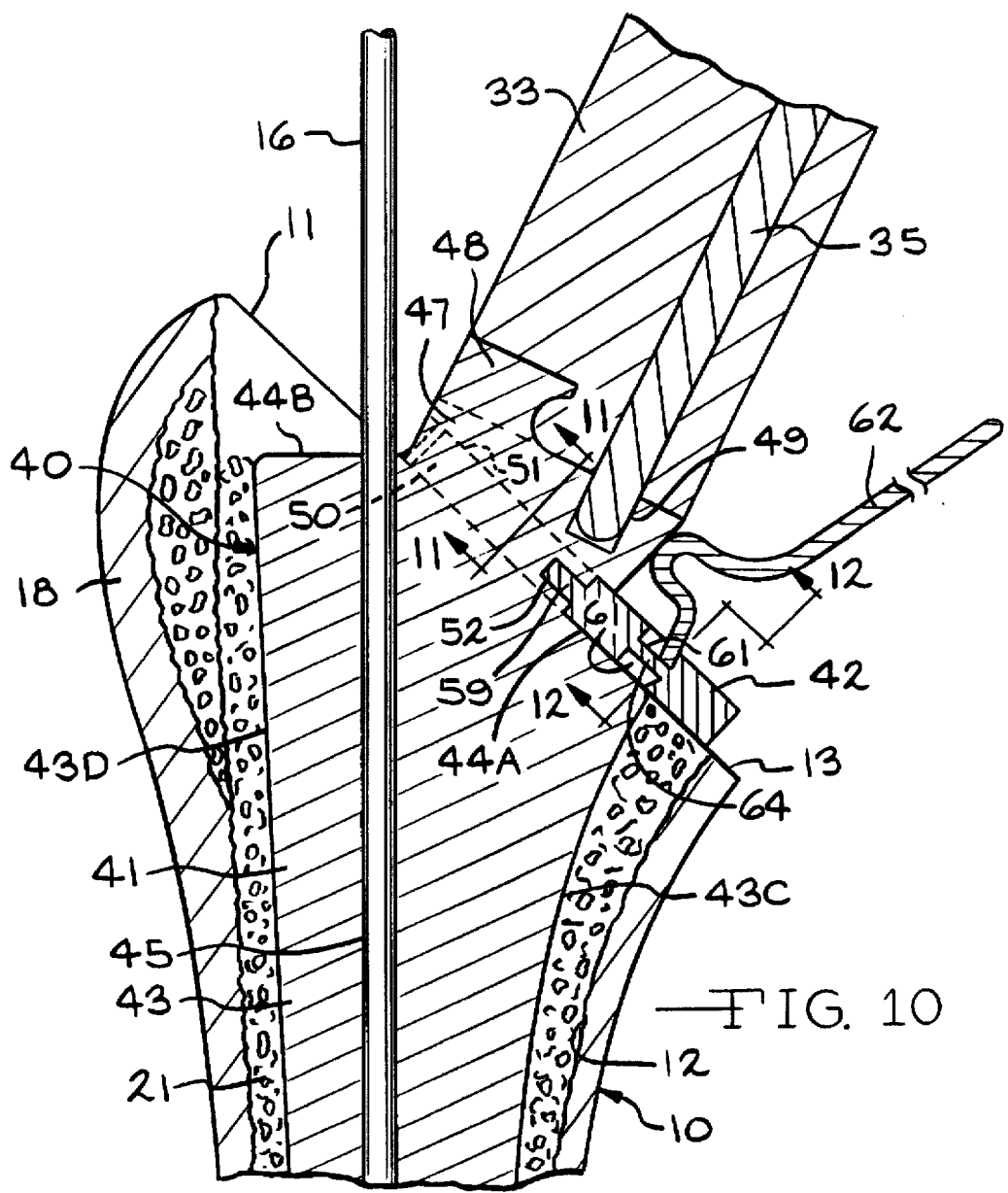
FIG. 10 is an enlarged fragmentary view of the proximal end of the tamp of FIG. 7 compacting bone graft material and showing a hook for removing the modular compressive flange member from the tamp member.

Among the advantages of the system and the method set forth in the present patent application, are accuracy, effectiveness of proximal graft compression, and reproducability on a consistent basis in preparing a cavity to receive a femoral hip joint prosthesis. The tamp of the present invention permits compaction of bone graft material completely to the plane defined by the proximal femoral cortices assuring that tight compaction of the graft material is achieved and that it may be precisely aligned with the proximal femoral cortices without damaging such cortices. Additionally, the system and the method of the present invention eliminates or at least greatly minimizes the possibility of fracturing the thin proximal femoral cortices which have been compromised during one or more previous hip surgeries.

Referring now to FIGS. 2 through 4, there is shown one embodiment of the present invention. There is shown a femur 10 having a proximal end 11 including the proximal femoral cortices. The femur 10 represents one which is previously had a femoral prosthesis (not shown) implanted therein which has been removed as part of the revision surgery process. Following removal of the previously implanted femoral prosthesis, an enlarged cavity 12 is reamed or otherwise formed to remove any debris and any old bone cement. One method of preparing the cavity 12 is disclosed and claimed in U.S. Pat. No. 5,047,035 of which I am also a co-inventor.

A restrictor 14 is positioned in the cavity 12 at the distal end. The restrictor 14 has a threaded cavity 15 in which is received one end of a guide wire 16 having a length sufficient to extend out of the proximal end 11 of the femur 10. Then, as may be seen from viewing FIG. 1, morsellized bone graft material 21 may be compacted in the distal end of the cavity 12 against the restrictor 14 using one or more cylindrical cannulated compactors 19 as is well known in the art. The cylindrical compactor 19 may be used to compact the bone graft material 12 in the distal end of the cavity 12 to about ⅓ to ½ the distance between the restrictor 14 and the proximal end 11.

A cannulated tamp generally designated by the numeral 20 is shown positioned in the cavity 12 being prepared to receive a new femoral prosthesis (not shown). Morsellized bone graft material 21 is shown being compacted by the tamp 20. The tamp 20 is made of a suitable metal such as stainless steel or an alloy of cobalt chrome molybdenum and includes a stem portion 22 extending from an upper proximal end 23 to a lower distal end 24. Preferably the stem portion 22 is polished to a smooth finish. The tamp 20 should have its stem 22 shaped similar to the shape of the femoral prosthesis intended to be implanted. If desired, a number of progressively larger tamps may be used until the morsellized bone graft material 21 is compacted to the desired density and the new cavity thus formed will be of the desired size. The largest size tamp 20 which is shown in FIGS. 2 through 4, will be larger than the prosthesis intended to be implanted by an amount which will permit new bone cement used to implant such prosthesis to have a thickness of two to four millimeters in all portions of the stem.

The tamp 20 has a longitudinal passageway 25 extending from the distal end 24 to the proximal end 23. The passageway 25 is sized to be positioned over the guide wire 16 and to slide freely thereon as it compacts the morsellized bone graft material 21. The proximal end 23 of the tamp 20 includes a first portion 23A which is disposed at an angle similar to the intended angle of cut of the proximal end 11 of the femur 10 and a second portion 23B, through which the passageway 25 extends, disposed at substantially right angles to such passageway 25.

As may be seen in FIGS. 3 and 4, the stem 22 has a series of surfaces extending distally from the proximal end 23 including an anterior surface 26, a posterior surface 27, a medial surface 28 and a lateral surface 29. As shown in FIGS. 2 and 3, in use the tamp 20 is oriented with the first portion 23A sloping toward the medial portion 13 of the proximal end 11 of the femur 10 and the second portion 23B extending toward the lateral portion 17 in the area of the greater trochanter 18. When the tamp 20 is so oriented, the posterior surface 27 will face the posterior portion 11A of the proximal end 11, the anterior surface 26 will face the anterior portion 11B of the proximal end 11, the medial surface 28 will face the medial portion 13 and the lateral surface 29 will face the lateral portion 17 and the greater trochanter 18.

In the embodiment of the invention shown in FIGS. 2–4, the tamp 20 is provided with an integral, monolithic proximal compressive flange 30 extending peripherally outwardly from the first portion 23A of the proximal end 23.

The flange 30 extends peripherally outwardly from the stem 22 a distance of 1 to 3 millimeters from the posterior surface 27 and the anterior surface 26 (see FIG. 4) and a distance of two to ten millimeters from the medial surface 28. (See FIG. 3).

Under the embodiment of FIGS. 2–4, the flange 30 does not extend to the area 23B of the tamp proximal end. The tamp should not have a flange in the vicinity of the stem lateral surface 29 as this surface faces the greater trochanter 18 which is susceptible to fracture or other damage if subjected to excessive compression of morsellized bone graft adjacent thereto or excessive impacts delivered to morsellized bone graft in an area adjacent thereto.

The tamp is also provided at its proximal end 23 with a protrusion 31 and knob 32 extending upwardly from the sloped first portion 23A of the tamp proximal end 23. The protrusion 31 and knob 32 may be engaged by a rasp handle 33 of any desired type for example, one manufactured by Zimmer, Inc., Warsaw, Ind., under its Item No. 6601-05. The protrusion 31 is provided with recess 34 for receiving a pin 35 of the rasp handle 33 in order to retain the rasp handle 33 on the tamp 20.

In preparing the femur 10 to receive the morsellized bone graft, small amounts of such bone graft material are placed in the enlarged cavity 12. In using the tamp combination 20 positioned over the guide wire 16, such morsellized bone graft material 21 is subjected to the forces imparted by impacts directed to the rasp handle 33. After appropriate amounts of such bone graft material are positioned in the cavity 12, the tamp is again subjected to impacts directed to the rasp handle 33, the force of such impacts going through the tamp 20 and effectively compacting the morsellized bone graft material 21. The bone graft material is compacted not only by the tapering exterior wall surfaces 26, 27, 28 and 29 of the tamp 22 but also by the proximal compressive flange 30. The presence of the flange 30 and the distally directed compressive forces imparted to the bone graft material 21 contacted thereby provides improved reliability of proper compaction density to the morsellized bone graft material than was possible under the tamp described in U.S. Pat. Nos. 5,192,283 and 5,470,336, including proper compaction density completely to the proximal end 11.

Under the embodiment of FIGS. 2-4 the tamp 20 is shown such that the extent to which the flange 30 extends outwardly from the stem 22 is limited to ensure that such flange 30 does not contact and damage the proximal end 11 of the femur 10 as the impacts are directed to the rasp handle. However, if desired, the flange 30 could have a greater outward extent and overlie the medial portion 13 and the anterior 11B and posterior 11A portions adjacent thereto to achieve proper compaction density of the bone graft material 21 completely to the proximal end 11 in those areas.

Figures 23, 24:
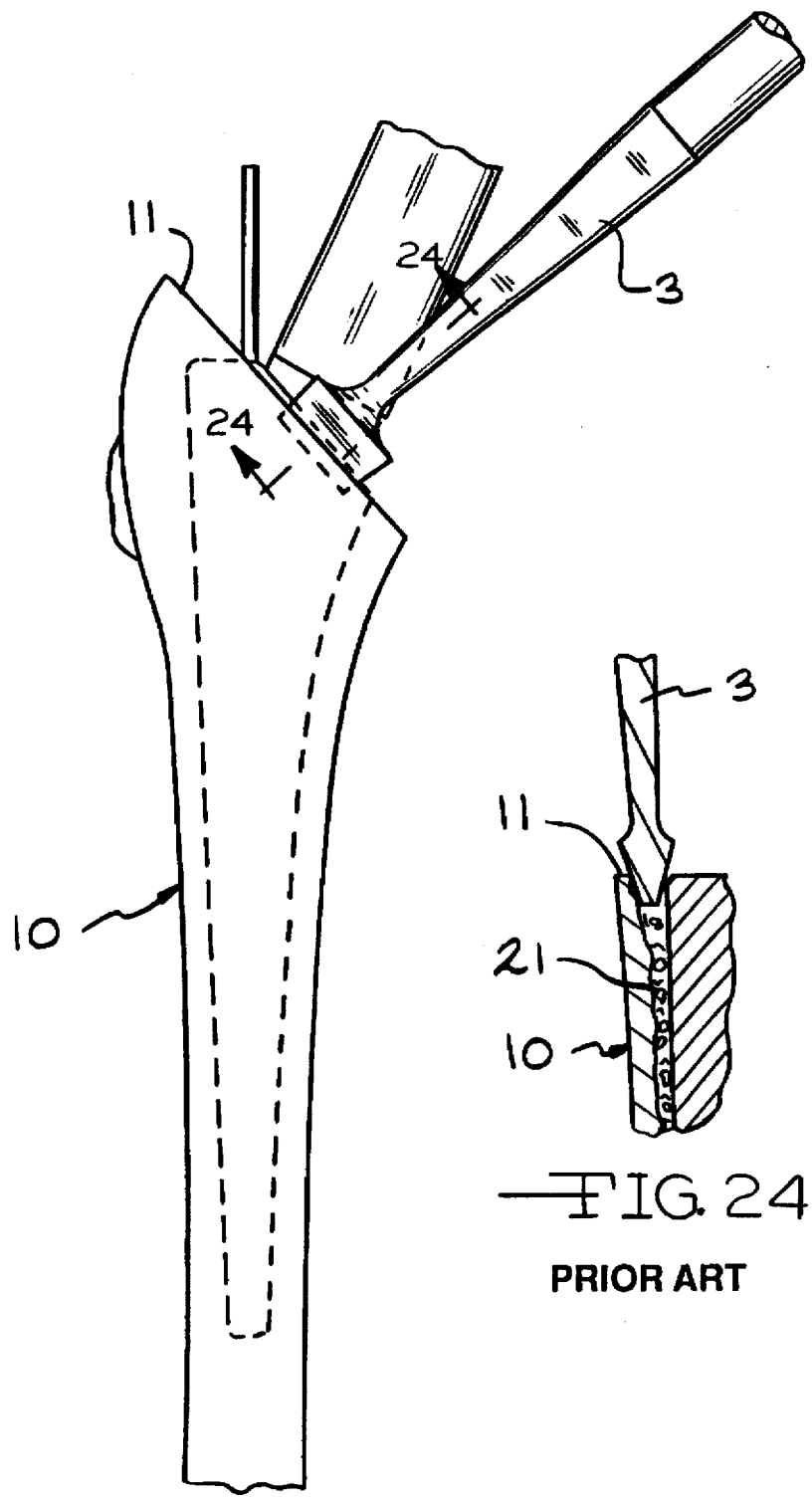
FIGS. 23 and 24 are views showing the use of a prior art small metal compactor compacting bone graft material in the gap between a prior art tamp and bone.

A comparison of the tamp and the method of the present invention and that of the prior art compaction at the proximal end of the femur may be had by viewing FIGS. 23 and 24, where a manually manipulated small metal compactor 3 is shown being utilized to compact the bone graft material 21 in the area of the proximal end 11 of the femur 10.

In actual practice, it is found that when the tamp 20 is properly positioned, the size of the gap between the interior wall of the cavity 12 of the femur and the anterior surface 26 may be greater or lesser than the gap between the interior wall of the cavity 12 and the posterior surface 27. It is, therefore, within the contemplation of the present invention that the flange 30 could be provided with a greater peripheral extent outwardly from the anterior surface 26 than from the posterior surface 27 or vice versa.

As shown in the embodiment of FIGS. 2-4, the flange 30 extends outwardly from the posterior surface 27 and the anterior surface 26 substantially equal distances and the central portion of the flange 30 extending from the medial surface 28 has a greater outward extent.

Referring now to FIGS. 5 and 6, there is shown a modified tamp 120 having an integral monolithic flange 101. Since the stem and most other portions of the modified tamp 120 other then the flange 101 are similar to the corresponding portions of the tamp 20 of the embodiment of FIGS. 2-4, they will not be described except to the extent necessary to describe the differences of the flange but rather will simply be provided with numerals which have a magnitude of 100 more than the corresponding portion of the embodiment of FIGS. 2-4.

The flange 101 of the embodiment of FIGS. 5 and 6 is provided with an extension 102 which extends beyond the first sloping portion 123A toward the lateral surface 129 a distance of 1 to 2 millimeters beyond the line of juncture 103 between such first sloping portion 123A and the second portion 123B of the proximal end 123. Preferably such extension 102 lies in the same plane as the remainder of the flange 101.

As can be seen particularly in FIG. 6, for those situations in which the gap between the interior wall of the cavity 12 and the anterior surface 126 in greater than the gap between the interior wall of the cavity and the posterior surface 127, the flange 101 may be provided with a first portion 104 extending from the anterior surface 126 having a greater outward extent than a second portion 105 extending from the posterior surface 127. Additionally, since such gaps are not necessarily of uniform breadth, the first portion 104 is shown as having a smaller outward extent in the vicinity of the extension 102 than in the vicinity of the medial surface 128. This is also true of the second portion 105.

Referring now to FIGS. 7-12, there is shown a modified tamp combination 40 including a tamp member 41 and a separately formed flange member 42 for engagement therewith. The tamp member 41, only a portion of which is shown, includes a stem 43 extending from a proximal end 44 to a distal end (not shown). The stem 43 includes an anterior surface 43A, a posterior surface 43B, a medial surface 43C and a lateral surface 43D. As in the previous embodiment, a passageway 45 extends from the distal end to the proximal end 44. The proximal end 44 includes a first portion 44A tapering at an angle toward the medial surface 43C and following substantially the intended angle at which the proximal end 11 of the femur 10 is cut and a second portion 44B. The passageway 45 extends from the distal end through the second portion 44B of the proximal end at substantially right angles to the second portion 44B.

A protrusion 47 extends from the first portion 44A of the proximal end and has an integral knob 48 formed thereon which is designed to be engaged by a rasp handle such as the rasp handle 33 described with reference to the embodiment of FIGS. 1 through 6. The protrusion 47 is provided with a cavity 49 sized to receive the pin 35 of the rasp handle 33. The protrusion 47 includes a pair of side walls 47A tapering toward one another in a direction away from the second section 44B and joined together at an arcuate nose 47B spaced from the cavity 49. The protrusion 47 is also provided with an undercut area 50 which is recessed inwardly from the tapering side walls 47A and from the nose 47B. A ledge 51 extends inwardly from the tapering side walls 47A and nose 47B to the undercut area 50. The ledge 51 is parallel to the first portion 44A of the proximal end and defines therewith a gap of substantially equal thickness throughout. A concavity 52 (see FIGS. 8 and 10) extends inwardly from that portion of the undercut area 50 underlying the nose 47B. Preferably the concavity has a rectangular cross sectional configuration; however, it could have any of a wide variety of cross sectional configurations.

The flange member 42 has a thickness permitting it to be snugly received in the undercut area 50, in the gap between the ledge 51 and the first portion 44A of the tamp proximal end 44. The tamp member 41 is provided with a notch 54 defining a pair of spaced apart legs 55A and 55B which extend from free ends 56A and 56B to a curved juncture 57 where they are joined. The legs 55A and 55B include inner surface portions 58 which taper inwardly toward one another and are joined at the curved juncture 57. A probe 59 having a size and cross sectional configuration matching that of the concavity 52 to permit its snug engagement therewith extends from the curved juncture towards the free ends 56A and 56B. The inner surface portions 58 and the curved juncture 57 are configured and sized to snugly engage the undercut area 50 throughout. When so engaged, the probe 59 will be snugly received in the concavity 52 thereby retaining the flange member 42 engaged to the tamp 40.

Optionally, each of the legs 55A and 55B may be provided with a detent 60 adjacent the free ends 56A and 56B extending inwardly toward the opposing leg. The detents 60 are sufficiently small in extent, on the order of less than 1 millimeter, to permit the legs 55A and 55B to flex outwardly a small amount as the flange 42 is slid through the gap and into engagement therein with the undercut area 50 of the protrusion 47. The detents 60 thereby provide an interference fit giving additional means for retaining the flange member 42 connected to the tapered tamp member 41.

The flange member 42 is also provided with an concavity 61 on each side separated by a web 64. The outwardly facing one of the concavities 61 may be engaged by a tool 62 (see FIGS. 10 and 12) when it is desired to replace the flange member 42 with a different sized flange member in order to accommodate the particular patient size and configuration of femur. It is within the contemplation of the invention that the web 64 could be omitted such that the concavities 61 would, in effect, be joined together to form a single aperture which could be engaged by a suitable removal tool such as the tool 62. However, it is preferred to have the web 64 as such web serves to prevent the bone graft material being compacted from escaping as it would from an aperture extending through the flange.

As previously described in connection with the embodiments of FIGS. 2 through 6, it is within the contemplation of the present invention that the flange 42 could be provided with a greater outward extent on the side extending from the anterior surface 43A than the side extending from the posterior surface 43B and vice versa. This may be seen particularly in FIGS. 8, 9 and 11 where the leg 55B has a breadth which, although of varying magnitude throughout its length from 56B to the curved juncture 57 is greater than the breadth of corresponding portions of the leg 55A. Such greater breadth results in the leg 55B having a greater outward extent from the anterior surface 43A than the outward extent of the leg 55A from the posterior surface 43B.

Figure 11:
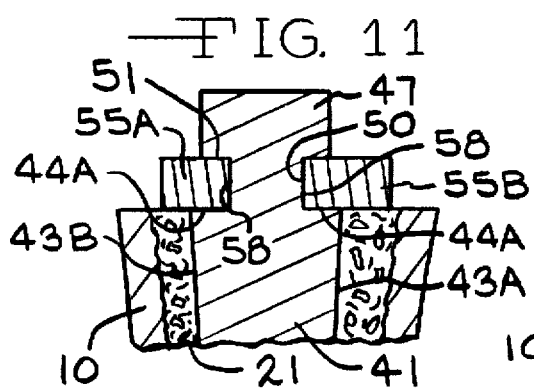
FIG. 11 is a sectional view taken through line 11—11 of FIG. 10.
Figure 12:
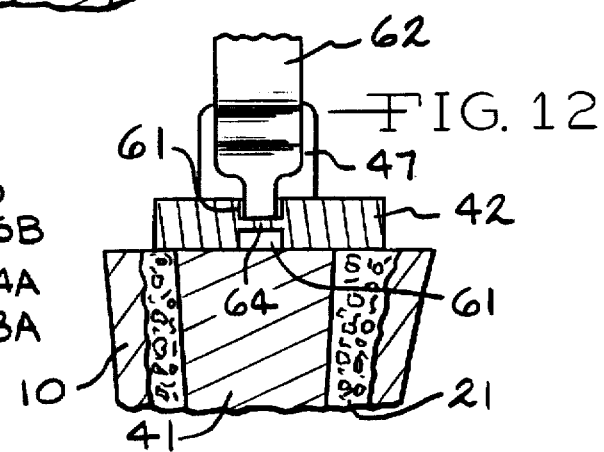
FIG. 12 is a sectional view taken through line 12—12 of FIG. 10.

As previously described, it will necessary to accommodate another patient having a greater sized gap between the posterior surface 43B and the inner bone surface of the cavity 12 than between the anterior surface 43A and the bone of the cavity of the anterior side. In that case, it will be desirable that the leg 55A have a greater breadth and outward extent than the leg 55B. In order to minimize the number of various sizes of and configurations of flange members required to be maintained in stock for various surgeries, the flange member 42 of the present invention is designed such that it may be reversible. In other words, the flange member 42 may be inserted in the slot 50 facing upwardly as shown in FIGS. 7, 8 and 11 with the leg 55B with its greater breadth providing a larger outward extent from the anterior surface 43A or, by simply turning it over, it may be readily positioned in the slot 50 with the result that the portion of the flange member leg having the greatest breadth and, therefore, outward extent will extend from the posterior surface 43B.

Figure 13:
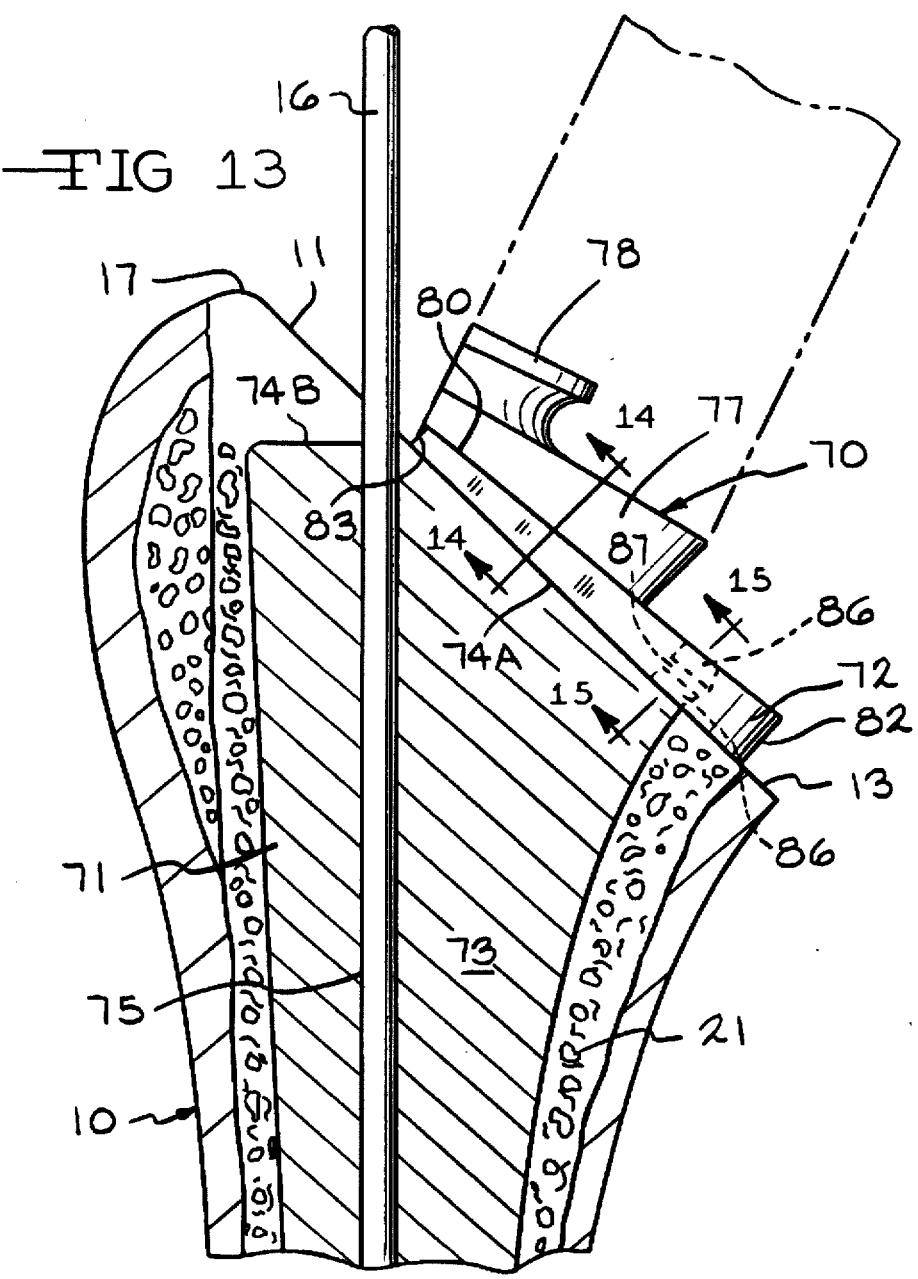
FIG. 13 is a view similar to FIG. 10 showing a further modified embodiment.
Figure 14:
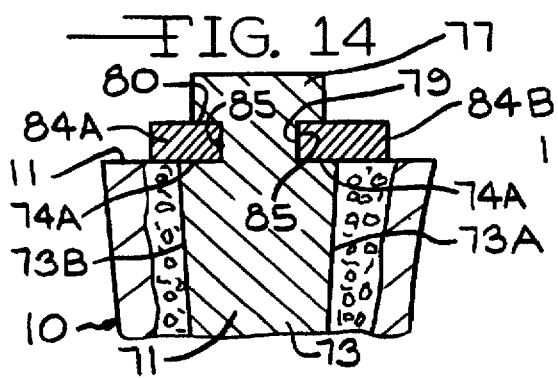
FIG. 14 is a sectional view taken through line 14—14 of FIG. 13.
Figure 15:
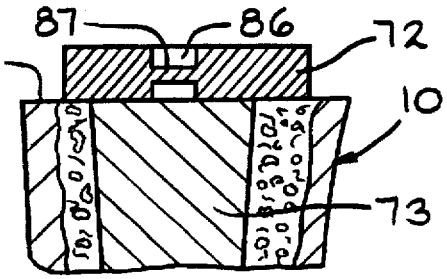
FIG. 15 is a sectional view taken through line 15—15 of FIG. 13.

Referring now to FIGS. 13–15, there is shown another embodiment under which there is provided a cannulated tamp combination 70 having a tapered tamp member 71 and a flange member 72. The tapered tamp member 71 has a stem 73 having proximal end with a first tapering portion 74A and a second portion 74B disposed at right angles to the cannulated passageway 75 sized to received the guide wire 16. A protrusion 77 having a knob 78 extends from the first proximal portion 74A. The protrusion 77 is provided with an undercut area 79 defining a ledge 80 spaced from the first portion 74A of the proximal end. The ledge 80 is spaced from the first portion 74A a greater distance in the area facing the medial side 13 of the proximal end 11 of the femur 10 than in the area facing the lateral side 17 of the femur thus providing a gap for the undercut 79 which tapers from a wider at the medial side 13 to narrower at the lateral side 17.

The flange member 72 is provided with a tapered thickness having a greater thickness at the curved juncture 82 adjacent such medial side 13 and tapering at the same degree of taper as the gap of the undercut area 79 toward the free ends 83 of the legs 84A and 84B. The legs 84A and 84B have inner surface portions 85 which follow the contour of the undercut area 79. However, under this embodiment, although there could be a probe and concavity similar to the probe 59 and concavity 61 of the embodiment of FIGS. 7–12, such a probe and concavity are unnecessary as retention of the flange member 72 in the gap between the ledge 80 and the first tapered proximal surface 74A is accomplished by the wedging action resulting from the tapering thickness of the flange member and the matching taper of the gap defined by the ledge 80 and such proximal end first portion 74A.

As is the embodiment of FIGS. 7–12, the legs 84A and 84B may be formed with unequal breadths. As shown in FIG. 14 the leg 84B is provided with a greater breadth than the leg 84A with the result that the outward extent of the leg 84B from the anterior surface 73A of the stem 73 is greater than the outward extent of the leg 84A from the posterior surface 73B. The flange 72 member of the present embodiment is reversible and may be turned over to position the leg 84B to have a greater outward extent the posterior side 73B of the stem 73. The flange member 72 may be provided with concavities 86 separated by a web 87 as in the previous embodiment.

Referring now to the embodiments of FIGS. 16–18, there is provided yet another embodiment of cannulated tamp combination 90. In this embodiment, there is provided tapered tamp member 91 having a stem 93 extending to a proximal end having a tapered first portion 94A and a second portion 94B disposed at substantially right angles to a passageway 95 sized to receive a guide wire.

A protrusion 97 having a knob 98 extends from the first proximal end portion 94A. The protrusion 97 is provided with a pair of parallel side walls 99, a medial end wall 100A and a lateral end wall 100B. Each of the side walls 99 has a dove-tail groove 89 formed therein extending from the medial end wall 100A to the lateral end wall 100B. As a result of the dove-tail configuration, each of the grooves 89 is tapered as shown in FIG. 17 such that the bottom or inside of the groove 89 is wider than the portion at the side wall 99.

The tamp combination 90 of this embodiment is provided with a flange member 140 having a pair of spaced apart leg portions 141A and 141B which extend from free ends 142 to a closed area of juncture 143. Each of the legs 141A and 141B has a tongue 144 extending inwardly toward the opposing leg. The tongues 144 are shaped and sized to be slidably received in the grooves 89 of the parallel side walls 99, thus provide means for securing the flange member 140 to the tamp member 91. If desired, the medial end wall 100A of the protrusion 97 may be provided with a concavity 88. The concavity 88 may have any desired cross-sectional configuration such as rectangular, oval or circular, but preferably tapers from a larger size at the medial end wall 100A to a smaller cross-sectional size inwardly therefrom. If such option is used, the flange member 140 will have a tapered probe 145 extending from that portion of the juncture area 143 intending to engage the medial end wall 100A. The probe 145 should be tapered and sized to become wedged in the concavity 88.

If desired, the legs 141A and 141B could be of identical configuration and breadth, however, they have been shown with the leg 141B having a greater breadth than the leg 141A. The flange member 140 of this embodiment is also reversible for those flange members in which the legs 141A and 141B have different breadths extents.

If desired, the flange member 140 may be formed in two pieces having mating faces extending through the area of juncture 143 and probe 145 as indicated by the dashed line 146 in FIG. 18.

As will be readily appreciated, if desired, instead of having the grooves 89 formed in the side walls 99 of the protrusion 97 and the tongues 144 extending from the legs 141A and 141B, the side walls 99 could be provided with tongues and the legs 141A and 141B provided with grooves sized to receive such tongues.

Figure 19:
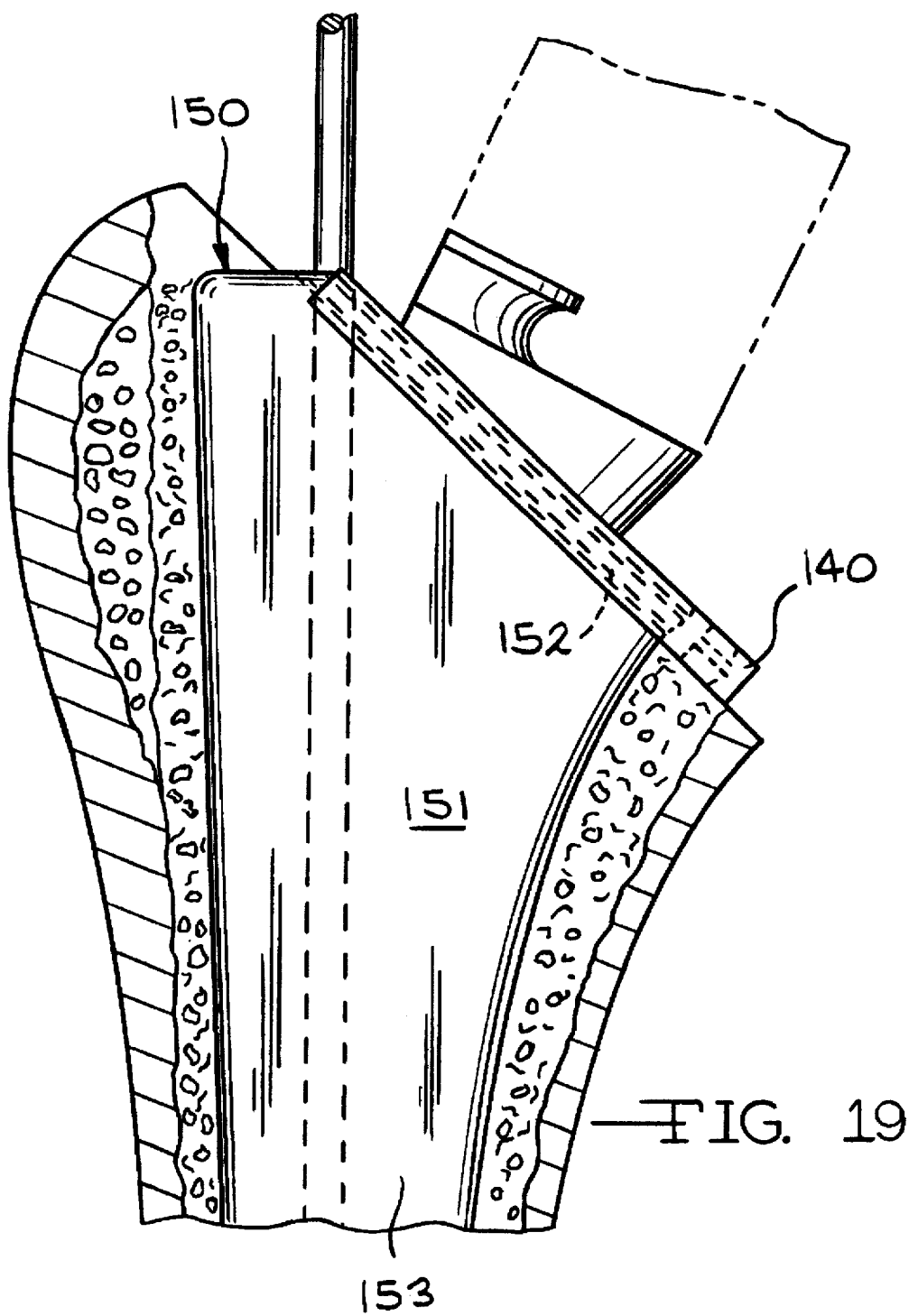
FIG. 19 is a view similar to FIG. 16 showing another embodiment.

Referring now to FIG. 19, there is provided a further embodiment. In this embodiment there is provided a tamp combination 150 having a tapered tamp member 151 and a flange member 140 identical to the flange member of the embodiment of FIGS. 16-18. Under this embodiment, is contrast to providing grooves in the protrusion such as the grooves 89 formed in the protrusion 97 in the previous embodiment, grooves 152 are formed in the stem 153 of the tamp member 151 the tongues 144 of the legs 141A and 141B of the flange 140 will be received in the grooves 152 of the stem 153.

If desired, instead of having the grooves 152 formed in the stem 153 and the tongues 144 extending from the legs 141A and 141B, the stem 153 could be provided with tongues and the legs 141A and 141B provided with grooves sized to receive such tongues.

Figures 20, 21, 22:
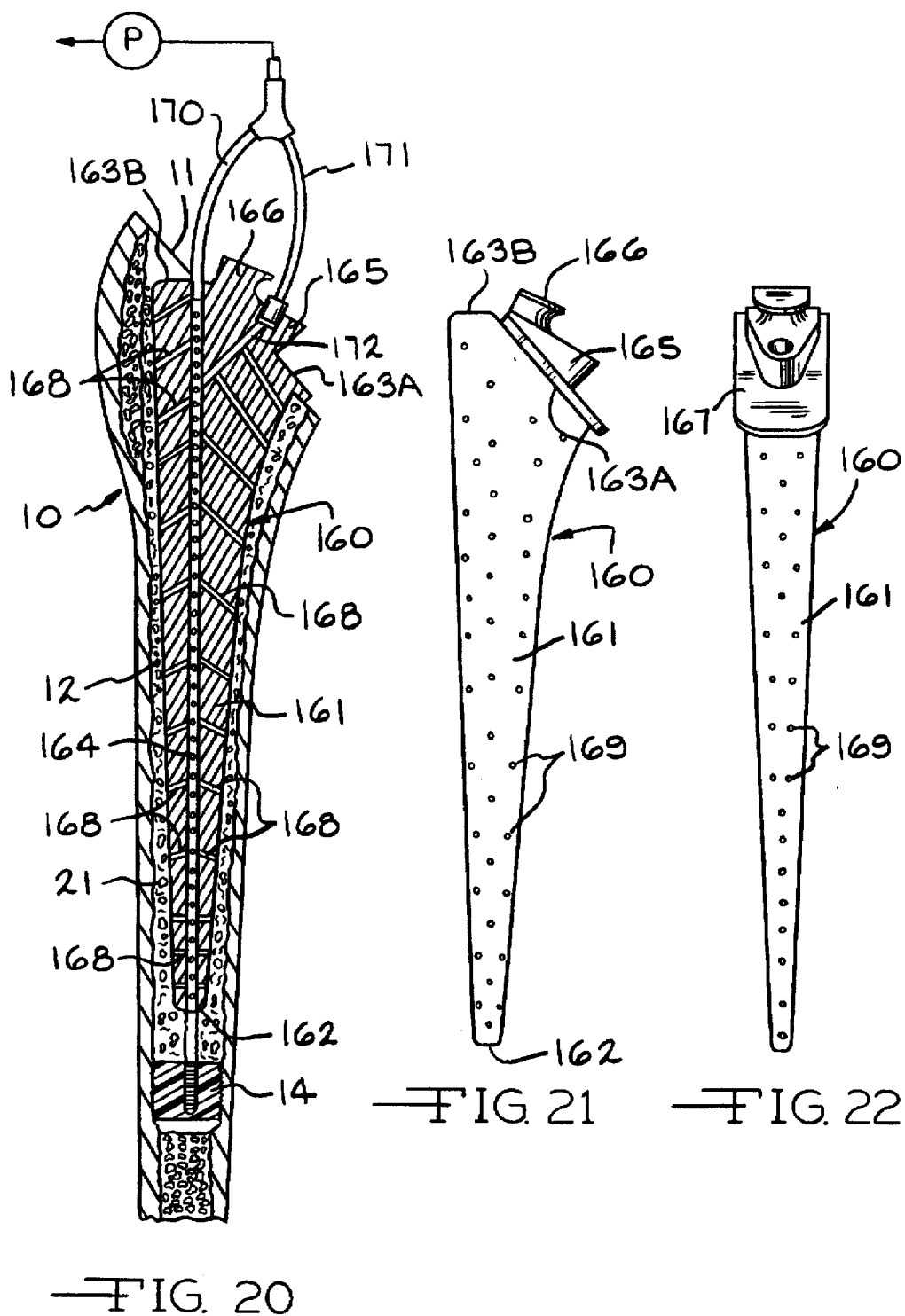
FIG. 20 is a sectional view of a cannulated tamp with an integral compressive flange and a plurality of passageways extending to a large number of apertures in its exterior surface.
FIG. 21 is an elevational view of the cannulated tamp of FIG. 20.
FIG. 22 is an end view showing the cannulated tamp of FIG. 20 rotated 90° from the position of FIG. 21.

Referring now to FIGS. 20-22, there is provided yet another embodiment of tamp 160 which may be utilized to drain blood and other liquids from the cavity being prepared. There is thus provided a tamp 160 having a tapered stem 161 extending from a distal end 162 to a proximal end 163. A cannulation passageway 164 extends from the distal end 162 to the proximal end 163. The cannulation passageway 164 may be sized to receive guide wire. The proximal end 163 has a first portion 163A which tapers at an angle similar to the angle of cut at the proximal end 11 of the femur 10 and a second portion 163B disposed at substantially right angles to the cannulation passageway 164. A protrusion 165 having a knob 166 extends from the first portion 163A of the proximal end. Additionally, a flange 167 extends outwardly from the first tapered portion 163A of the stem 161.

The stem 161 is provided with a network of connector passageways 168 extending from apertures 169 at the surface of the stem 161 to the cannulation of passageway 164. Upon completion of compacting the bone graph material 21, the guide wire may be removed and a vacuum line 170 connected to a source of vacuum may be attached to the cannulation passageway 164. If desired a second vacuum line 171 may be attached an additional passageway 172 extending to the protrusion 165. Vacuum applied through the vacuum lines 170 and 171 will serve to remove blood and other fluid from the newly formed cavity defined by the compacted bone graft material.

Although the tamp 160 of the embodiment of FIGS. 20-22 has been shown with an integral flange 167 which is monolithic with the stem 161, it is within the contemplation of this embodiment that the series of passageways 164, 168 and 172 could be used with a tamp member having a modular flange such as those described in the embodiments of FIGS. 7-19 or could be used with a tamp having no flange or flange member whatsoever.

Although it is preferred that the tamp with proximal compressive flange of the present invention be used with a stem having a cannulation or passageway to receive a guide wire, it is clearly possible and within contemplation of the present invention that the proximal compressive flange could be used with a wide variety of tamps including ones not having a cannulation. Additionally, although the tamp members have been shown with one configuration of knob and protrusion, other configurations may be used. Additionally, although a number of types of means for attaching the modular flange members to the tamp members, it is within the contemplation of the present invention that a wide variety of designs of attachment members could be utilized for attaching the modular flange members to the tamp members.

Many modifications will become readily apparent to those skilled in the art. Accordingly, the scope of the present invention should be determined only by the scope of the claims appended hereto.

I claim:

1. In combination with handle having an impacting surface, a tamp for compacting bone graft material in a femur being prepared to receive a femoral prosthesis comprising:

(a) a tapered stem extending from a distal end in increasing cross-sectional size to a proximal end, said stem having anterior, posterior, medial and lateral surfaces adjacent said proximal end, said proximal end having a handle engagement rail extending therefrom; and (b) a flange extending outwardly from major portions of said anterior, posterior and medial surface for compacting bone graft material.

2. A tamp according to claim 1 wherein said stem has a passageway extending from said distal end to said proximal end.

3. A tamp according to claim 2 wherein said flange is monolithic with said stem.

4. A tamp according to claim 3 wherein said flange extends outwardly from one of said posterior or anterior surfaces a greater distance than from the other of said posterior or anterior surfaces.

5. A tamp according to claim 3 wherein said flange extends outwardly from said posterior and said anterior surfaces a distance of one to three millimeters and outwardly from said medial surface a distance of two to ten millimeters.

6. A tamp according to claim 5 wherein said flange extends outwardly from one of said posterior and said anterior surfaces a greater distance that from the other of said posterior or anterior surfaces.

7. A tamp according to claim 1 wherein (a) said stem proximal end has a first portion extending from said anterior, posterior and lateral surfaces and a second portion extending from said anterior, posterior and medial surfaces at an angle relative to said first portion, (b) said stem has a passageway extending from said distal end to said proximal end first portion and (c) said flange extends beyond said second portion to a position overlying said first portion.

8. A tamp according to claim 7 wherein said flange is a separately formed, modular unit affixed on said stem proximal end second portion.

9. A tamp according to claim 8 wherein said flange extends outwardly from one of said posterior or anterior surfaces a greater distance than from the other of said posterior or anterior surfaces.

10. A tamp according to claim 8 wherein said flange extends outwardly from said posterior and said anterior surfaces a distance of one to three millimeters and outwardly from said medial surface a distance of two to ten millimeters.

11. A tamp according to claim 10 wherein said flange extends outwardly from one of said posterior and said anterior surfaces a greater distance than from the other of said posterior or anterior surfaces.

12. In combination with a handle having an impacting surface, a tamp for compacting bone graft material in a femur being prepared to receive a femoral prosthesis comprising:
(a) a tapered stem extending from a distal end in increasing cross-sectional size to a proximal end, said stem having anterior, posterior, medial and lateral surfaces adjacent said proximal end and a passageway extending from said distal end to said proximal end, a protrusion extending from said proximal end, said protrusion including a handle engaging rail, a recessed area adjacent said proximal end and an enlarged area spaced from said proximal end defining a shoulder; and
(b) a modular flange for compacting bone graft material engaged to said protrusion in said recessed area and extending outwardly beyond said anterior, posterior and medial surfaces a distance not to exceed the thickness of bone graft material as measured from each of said anterior, posterior and medial surfaces, respectively.

13. A tamp according to claim 12 wherein said flange extends outwardly from said posterior and said anterior surfaces a distance of one to three millimeters and outwardly from said medial surface a distance of two to ten millimeters.

14. A tamp according to claim 13 wherein said flange extends outwardly from at least one of said posterior and said anterior surfaces a greater distance than from the other of said posterior or anterior surfaces.

15. A tamp according to claim 12 wherein said flange extends outwardly from one of said posterior or anterior surfaces a greater distance than from the other of said posterior or anterior surfaces.

16. A tamp according to claim 12 wherein said modular flange has spaced apart first and second surfaces and may be removed from said stem, inverted from a position in which said first surface is closest to said proximal end to a position in which said second surface is closest to said proximal end, said flange extending outwardly from said posterior surface a greater distance when said first surface is closest to said proximal end and outwardly from said anterior surface a greater distance when said second surface is closest to said proximal end.

17. A tamp according to claim 12 wherein said recessed area defines (i) a pair of sidewall portions tapering inwardly in a direction toward said medial surface and (ii) a connector portion facing said medial surface extending between said sidewall portions and said flange has (a) a pair of legs with inwardly facing walls engaging said sidewall portions and (b) an end portion from which said legs extend, said end portion including an end wall engaging said connector portion.

18. A tamp according to claim 17 wherein said recessed area is provided with a cavity inwardly from said connector portion and said flange is provided with a probe extending from said end wall and received in said cavity.

19. A tamp according to claim 17 wherein each of said legs inwardly facing walls extend to an opposing free end and is provided with a detent at said opposing free end engaged to said protrusion.

20. A tamp according to claim 17 wherein the shoulder of said protrusion is spaced from said proximal end a greater distance in the area facing said medial surface and tapers to a smaller distance as it extends away from said medial surface and said flange is thicker at said end portion than at said opposing free ends.

21. A tamp according to claim 12 wherein said recessed area defines (i) a pair of sidewall portions parallel to one another and (ii) a connector portion facing said medial surface extending between said sidewall portions and said flange has (a) a pair of legs with parallel inwardly facing walls engaging said sidewall portions and (b) an end portion from which said legs extend, said end portion including an end wall engaging said connector portion.

22. A tamp according to claim 21 wherein each of said sidewall portions has a groove extending from said connector portion and each of said legs has an outwardly extending tongue slideably received in said groove.

23. A tamp according to claim 21 wherein each of said sidewall portions has an outwardly directed tongue and each of said legs has a groove slideably receiving said tongue.

24. A tamp according to claim 21 wherein said recessed area is provided with a cavity inwardly from said connector portion and said flange is provided with a probe extending from said end wall and received in said cavity.

25. A tamp according to claim 21 wherein said flange consists of multiple, separately formed pieces.

26. A tamp according to claim 12 wherein said stem has a groove in each of said anterior surface and said posterior surface and said flange has (a) a pair of legs with parallel inwardly facing walls, each having a tongue engaged in a groove and (b) an end portion from which said legs extend, said end portion including an end wall engaging said medial surface.

27. A tamp according to claim 26 wherein said stem is provided with a cavity inwardly from said medial surface and said flange is provided with a probe extending from said end wall and received in said cavity.

28. A tamp according to claim 12 wherein said stem has a tongue extending from each of said anterior surface and said posterior surface and said flange has (a) a pair of legs with parallel inwardly facing walls, each having a groove receiving one of said tongues and (b) an end portion from which said legs extend, said end portion including an end wall engaging said medial surface.

29. A tamp according to claim 28 wherein said stem is provided with a cavity inwardly from said medial surface and said flange is provided with a probe extending from said end wall and received in said cavity.

30. In combination with a handle having an impacting surface, a tamp for compacting bone graft material in a femur being prepared to receive a femoral prosthesis comprising:
(a) a tapered stem extending from a distal end in increasing cross-sectional size to a proximal end, said stem having anterior, posterior, medial and lateral surfaces adjacent said proximal end, a central passageway extending from major portion of said distal end to said proximal end and a plurality of connector passageways extending between said central passageway and said anterior, posterior, medial or lateral surface, said proximal end having a handle engaging rail extending therefrom; and (b) a flange extending outwardly from said anterior, posterior and medial surfaces for compacting bone graft material.

31. A tamp according to claim 30 further including a source of vacuum for drawing fluid from said central passageway and said connector passages.

32. A method of preparing a medullary canal of a femur for implantation of a hip prosthesis having a stem portion of predetermined configuration wherein said femur has a surgically prepared proximal end and a prepared cavity larger than said predetermined configuration extending distally from said proximal end comprising:

(a) placing bone graft material in said cavity;

(b) providing a tamp having a stem extending from a proximal end to a distal end and having a configuration similar to said predetermined configuration and having a passageway extending through said stem from said distal end to said proximal end, said tamp having a flange extending outwardly from said stem at said stem proximal end;

(c) positioning a guidewire in said cavity;

(d) placing said tamp over said guidewire with the guidewire extending through said passageway;

(e) impacting said tamp against said bone graft material with said stem and said flange to compact said bone graft material substantially to said prepared proximal end to form a prosthesis receiving cavity, said flange being of such dimension as permit said compacting without said flange contacting said prepared proximal end.

33. A method of preparing a medullary canal of a femur according to claim 32 further including apply a vacuum through said passageway to draw fluid from said cavity.

34. The method according to claim 32 wherein said flange is monolithic with said stem.

35. The method according to claim 32 wherein said tamp has anterior, posterior, medial and lateral surfaces and said flange extends outwardly from one or said posterior or anterior surfaces a greater distance than from the other of said posterior or anterior surfaces.

36. The method according to claim 32, wherein said tamp has anterior, posterior, medial and lateral surfaces and said flange extends outwardly from said posterior and said anterior surfaces a distance of one to three millimeters and outwardly from said medial surface a distance of two to ten millimeters.

37. The method according to claim 32 wherein said flange is a separately formed, modular unit affixed on said stem proximal end second portion.

38. The method according to claim 37, wherein said tamp has anterior, posterior, medial and lateral surfaces and said flange extends outwardly from one of said posterior or anterior surfaces a greater distance than from the other of said posterior or anterior surfaces.

\* \* \* \* \*

UNITED STATES PATENT AND TRADEMARK OFFICE
CERTIFICATE OF CORRECTION

PATENT NO. : 5,683,395
DATED : November 4, 1997
INVENTOR(S) : W. E. Michael Mikhail It is certified that error appears in the above-identified patent and that said Letters Patent is hereby corrected as shown below:

Col. 10, line 55, delete "that" and insert --than--.

Col. 11, line 54, insert --extending-- before "outwardly".

Col. 13, line 1, insert --major portions of-- after "from".

Signed and Sealed this

Fourteenth Day of April, 1998

Attest:

BRUCE LEHMAN

*Attesting Officer*   *Commissioner of Patents and Trademarks*